US007223421B2

(12) United States Patent  (10) Patent No.: US 7,223,421 B2
McTeigue et al.  (45) Date of Patent: May 29, 2007

(54) TESTE MASKED PHARMACEUTICAL PARTICLES

(75) Inventors: Daniel McTeigue, N. Wales, PA (US); Narenda Parikh, Long Valley, NJ (US); David W. Wynn, Abington, PA (US); Ravivaj S. Pillai, Lansdale, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 445 days.

(21) Appl. No.: 09/878,034

(22) Filed: Jun. 8, 2001

(65) Prior Publication Data

US 2002/0031552 A1 Mar. 14, 2002

Related U.S. Application Data

(60) Provisional application No. 60/215,505, filed on Jun. 30, 2000.

(51) Int. Cl.
*A61K 9/28* (2006.01)

(52) U.S. Cl. .................. 424/497; 424/441; 424/494; 424/495; 424/490

(58) Field of Classification Search ................ 424/489, 424/490, 494, 495, 441, 497
See application file for complete search history.

(56) References Cited

U.S. PATENT DOCUMENTS

| 4,385,078 A | 5/1983 | Onda et al. |
| 4,749,575 A | 6/1988 | Rotman |
| 4,800,087 A | 1/1989 | Mehta |
| 4,916,161 A | 4/1990 | Patell |
| 4,940,588 A | 7/1990 | Sparks et al. |
| 4,952,402 A | 8/1990 | Sparks et al. |
| 4,971,791 A | 11/1990 | Tsau et al. |
| 5,084,278 A | 1/1992 | Mehta |
| 5,409,711 A | 4/1995 | Mapelli et al. |
| 5,536,507 A | 7/1996 | Abramowitz et al. |
| 5,614,220 A | 3/1997 | Hirakawa et al. |
| 5,681,584 A | 10/1997 | Savastano et al. |
| 5,814,332 A | 9/1998 | Ghanta et al. |
| 5,837,277 A | 11/1998 | Hayward |
| 6,046,177 A | 4/2000 | Stella et al. |
| 6,139,865 A | 10/2000 | Friend et al. |

FOREIGN PATENT DOCUMENTS

| CA | 2068366 A1 | 5/1992 |
| JP | 48103718 | 4/1972 |

OTHER PUBLICATIONS

Simone Shcmid et al., Enteric Coating of Ibuprofen Crystals Using Modified Mechacrylate Copolymers, Drugs and Science Technology, Drugs made in Germany 44, No. 1 (2001) pps 12–19.
International Search Report for EP 1166777 (MCP 0279) dated Oct. 10, 2001.

*Primary Examiner*—Neil S. Levy
(74) *Attorney, Agent, or Firm*—Michele G. Mangini

(57) ABSTRACT

Taste masked particles and chewable tablets made therefrom are disclosed. The taste masked particles comprise a core containing an active ingredient and a polymeric coating covering said core, said coating comprising a mixture of a) an enteric polymer; and b) an insoluble film forming polymer, the surface of said particle being free of active ingredient. The chewable tablets provide immediate release of the active ingredient.

20 Claims, No Drawings

TESTE MASKED PHARMACEUTICAL PARTICLES

This application claims the benefit of Provisional U.S. Patent Application No. 60/215,505 filed Jun. 30, 2000.

This invention relates to taste masked pharmaceutical particles comprising a polymeric coating that is a mixture of an enteric polymer and an insoluble film forming polymer. The coated particles may be used to make chewable tablets that surprisingly exhibit an immediate release profile.

BACKGROUND OF THE INVENTION

Pharmaceuticals intended for oral administration are typically provided in solid form as tablets, capsules, pills, lozenges, or granules. Tablets are swallowed whole, chewed in the mouth, or dissolved in the oral cavity. Chewable tablets are typically made from a mixture including active drug particles, and other inactive ingredients (excipients), and are often employed for the administration of pharmaceuticals where it is impractical to provide a tablet for swallowing whole. With chewable tablets, the act of chewing helps to break up the tablet particles as the tablet disintegrates and may increase the rate of absorption by the digestive tract. Chewable tablets are often utilized to improve drug administration in pediatric and geriatric patients.

Certain drug particles have a bitter or otherwise unpleasant taste. In order to make chewable tablets from these, their taste must be masked for example by dispersing or coating the particles with a coating composition. Depending on the nature of the coating composition, the dissolution or release profile of the particles and tablets made therefrom can be changed.

For example, U.S. Pat. No. 5,536,507 to Abramowitz et al. relates to a three component pharmaceutical formulation containing one or more pharmacologically active substances such that greater than 80% of the active substance will be released in the large intestine. The formulation comprises a core comprising the pharmacologically active substance, microcrystalline cellulose, a pH-sensitive polymer, and optionally an osmotic agent. Over the core is a delayed release coating comprising a non-water soluble polymer such as Eudragit RS30D (poly(ethyl acrylate, methyl methacrylate)trimethylammonioethyl methacrylate chloride)) or ethylcellulose, a plasticizer and an antiagglomerating agent. Over the delayed release coating is an enteric coating such as cellulose acetate phthalate, cellulose acetate trimetallate, or Eudragit L30D (poly(methacrylic acid, ethyl acrylate)).

U.S. Pat. No. 5,681,584 to Savastano et al. relates to another delayed release drug delivery device. In this case, the targeted site for drug delivery is within the gastrointestinal tract, particularly the colon. The device consists of a solid core comprising an active ingredient coated with three separate layers: 1) a delay jacket comprising a binder, an osmotic agent and a lubricant; 2) a semipermeable membrane that may be made of cellulose acetate, ethyl cellulose, cellulose acetate phthalate, or Eudragit NE30D (poly(ethyl acrylate, methyl methacrylate)), Eudragit RL (poly(ethyl acrylate, methyl methacrylate)trimethylammonioethyl methacrylate chloride) or Eudragit RS (poly(ethyl acrylate, methyl methacrylate)trimethylammonioethyl methacrylate chloride); and 3) an enteric polymer such as cellulose acetate phthalate or hydroxypropyl methylcellulose phthalate.

Canadian Appln. No. 2,068,366 describes a microcapsule composition and process for making the same. The dissolution profile of the microcapsule is reduced by approximately 25%, preferably approximately 40%, more preferably approximately 50%, relative to a standard microencapsulated tablet when measured at a pH of about 6.8. The microcapsule composition of Canadian Appln. No. 2,068,366 is made by spray drying a suspension or dispersion of a pharmaceutically active ingredient in a coating solution. The coating solution contains 3 to 75 wt % of a water insoluble polymer. The coating solution may optionally contain an enteric, reverse enteric, or water soluble polymer as well. In Example 3 of the application, an enteric coating comprising ethylcellulose, hydroxypropyl methylcellulose acetate succinate and dichloromethane was spray dried with sodium diclofenac. The release profile of the enteric coated diclofenac, shown in FIG. 3, indicates that less than 80% of the drug had been released after 30 minutes in a pH 7.5 solution.

U.S. Pat. No. 4,800,087 to Mehta relates to taste-masked pharmaceutical compositions in which pharmaceutically active compound is microencapsulated with a polymer coating. The polymer coating comprises a high temperature film forming polymer in combination with either a plasticizer or a low temperature film forming polymer. The high temperature film forming polymer may be ethyl cellulose or another cellulose polymer or preferably Eudragit L30D, which is an enteric polymer. The low temperature film forming polymer is preferably Eudragit NE30D, which is a nonenteric polymer that swells in aqueous solution.

Applicants have now discovered that taste masked pharmaceutical formulations having an immediate release profile may be made using a continuous polymeric coating comprising a mixture of an enteric polymer and an insoluble film forming polymer. The polymeric coating is used to cover the entire surface of drug particles, such that the surfaces of the particles are substantially free of active ingredient. The coated particles of the invention advantageously exhibit sufficient elasticity without the need for plasticizer to maintain integrity during tableting and prevent release of the drug into the mouth during chewing. Chewable tablets made from these coated particles have excellent taste and yet surprisingly exhibit an immediate release profile.

SUMMARY OF THE INVENTION

The present invention provides a taste masked particle comprising a core containing an active ingredient and a polymeric coating covering said core, said coating comprising a mixture of a) an enteric polymer; and b) an insoluble film forming polymer, the surface of said particle being free of active ingredient.

The invention also provides a chewable tablet comprising a granular agglomerate of taste masked particles, each particle comprising a core containing an active ingredient and a polymeric coating covering said core, said coating comprising a mixture of a) an enteric polymer; and b) an insoluble film forming polymer, the surface of said particle being free of active ingredient.

The invention further provides a method of taste masking particles comprising an active ingredient, which comprises applying a continuous polymeric coating over said particles, said coating comprising a mixture of a) an enteric polymer; and b) an insoluble film forming polymer.

DETAILED DESCRIPTION OF THE INVENTION

The core of the taste masked particle may comprise any one of a number of active ingredients. Suitable active ingredients broadly include analgesics, decongestants, expectorants, antitussives, antihistamines, gastrointestinal agents, diuretics, bronchodilators, sleep-inducing agents, vitamin and mineral supplements, anti-infectives, and mixtures thereof, in particular those with an unpleasant taste. One class of preferred active ingredients include nonsteroidal anti-inflammatory drugs (NSAIDs), such as ibuprofen, ketoprofen, flurbiprofen, naproxen, diclofenac, rofecoxib, celecoxib, and aspirin. The active ingredient may alternatively be selected from acetaminophen, pseudoephedrine, phenylpropanolamine, chlorpheniramine, dextromethorphan, diphenhydramine, dimenhydrinate, meclizine, famotidine, loperamide, ranitidine, cimetidine, astemizole, loratadine, desloratadine, fexofenadine, cetirizine, antacids, mixtures thereof and pharmaceutically acceptable salts or metabolites thereof. Most preferably, the active ingredient is selected from the group consisting of acetaminophen, ibuprofen, pseudoephedrine, dextromethorphan, diphenhydramine, chlorpheniramine, loratadine, calcium carbonate, magnesium hydroxide, magnesium carbonate, magnesium oxide, aluminum hydroxide, mixtures thereof, and pharmaceutically acceptable salts thereof.

The core of the particle may comprise pure, crystalline active ingredient, or a mixture of active ingredient with optional ingredients, such as binders, excipients and the like known in the art. The core may be formed using a variety of well known granulation methods, including high sheer wet granulation, spray drying, and fluid bed granulation (including rotary fluid bed granulation). Preferably, the particle core is made by fluid bed granulation.

The polymeric coating covers the core. The polymeric coating comprises a mixture of a) an enteric polymer and b) and insoluble film forming polymer. The enteric polymer may be selected from any one of a variety of known enteric polymers, such as hydroxypropyl methylcellulose phthalate, hydroxypropyl methylcellulose acetate succinate, cellulose acetate phthalate, polyvinylacetate phthalate, and polymethacrylate-based polymers such as poly(methacrylic acid, methyl methacrylate) 1:2 (commercially available from Rohm Pharma GmbH as Eudragit S polymers), and poly(methacrylic acid, methyl methacrylate) 1:1 (commercially available from Rohm Pharma GmbH as Eudragit L polymers). Combinations of enteric polymers may also be used.

Preferably, the enteric polymer is selected from non-acrylate compounds, specifically hydroxypropyl methylcellulose phthalate, hydroxypropyl methylcellulose acetate succinate, cellulose acetate phthalate, and polyvinylacetate phthalate. Non-acrylates are preferred because acrylate polymers tend to become tacky and agglomerate at high temperature. Cellulose polymers are more heat stable than acrylate polymers. In addition, acrylate polymers are known to have a characteristic, slightly unpleasant taste, whereas cellulose polymers have a more neutral taste profile.

The insoluble film forming polymer may also be selected from a number of known compounds, including cellulose acetate, ethylcellulose, and poly(ethyl acrylate, methyl methacrylate, trimethylammonioethyl methacrylate chloride) 1:2:0.1 (commercially available from Rohm Pharma as Eudragit RS). One or more than one insoluble film forming polymer may be used. Preferably, the insoluble film forming polymer is impermeable and does not swell in an aqueous environment. More preferably, the insoluble film forming polymer is selected from cellulose acetate and ethylcellulose.

The weight ratio of enteric polymer to insoluble film forming polymer in the polymeric coating is preferably in the range of about 20:80 to about 80:20, more preferably about 40:60 to about 70:30.

The polymeric coating may comprise other optional ingredients. Preferably, the polymeric coating includes one or more non-enteric, water soluble polymers, such as hydroxypropyl cellulose and poly(ethyl acrylate, methyl methacrylate) (commercially available from Rohm Pharma GmbH as Eudragit NE 30D). When a non-enteric, water soluble polymer is present in the polymeric coating, the level of non-enteric, water soluble polymer is preferably about 10 to about 30% of the polymeric coating.

The polymeric coating also preferably comprises a surfactant. Suitable surfactants include both ionic and non-ionic materials from both synthetic and natural origins, including but not limited to lecithin, glyceryl esters, sugar esters, polysorbates, mono and diglycerides of fatty acids, propylene glycol esters, sucrose fatty acid esters and polyoxyethylene derivatives of sorbitan fatty acid esters. Examples of useful polysorbates include sorbitan trioleate, sorbitan monopalmitate, sorbitan monolaurate, propylene glycol monolaurate, glycerol monostearate, diglycerol monostearate, glycerol lactyl-palmitate. Lactic acid derivatives include sodium stearoyl lactylate and calcium stearoyl lactylate. When a surfactant is present in the polymeric coating, the level of surfactant is preferably about 2 to about 10% of the polymeric coating.

A particularly preferred polymeric coating comprises about 53 wt % hydroxypropyl methylcellulose phthalate, about 43 wt % cellulose acetate, and about 4 wt % polysorbate.

Advantageously, the present polymeric coating requires no plasticizer but still maintains elasticity sufficient to prevent rupture during tableting and chewing. Although plasticizers are commonly incorporated into known coating systems, they increase the cost and processing complexity of such systems. Importantly, they are also known to impart unpleasant oily tastes to coating systems. This is avoided with the present invention.

The polymeric coating is preferably applied to the particle core in the form of a solution using fluidized bed technology, such as Wurster coating or rotor coating. Useful solvents for this purpose include acetone and water at a ratio from about 85:15 to about 95:5.

In order to achieve complete tastemasking, it is important that the polymer coating be continuous and cover the entire surface of the core, so that little or no active ingredient is exposed. Exposed active ingredient is susceptible to dissolution in the oral cavity, where once in solution, it will be detected by the taste buds. Using the method of the present invention, it is now possible to completely eliminate the perception of "burn" associated with ibuprofen, for example. Coating methods such as spray-drying, that result in a matrix of active ingredient and coating, will result in inferior taste-masking because spray dried particles are usually porous and may have drug protrusions on the surface.

The thickness of the polymeric coating on the core is typically from about 1 to about 20 microns, preferably from about 2 to about 15 microns, and more preferably from about 4 to about 9 microns. The polymeric coating preferably forms about 5 to about 50, more preferably about 15 to about 25 weight percent of the taste masked particle.

Chewable tablets may be made by compacting a mixture including the taste masked particles. Several tableting methods are known in the art, including for example the use of compacting roller technology such as a chilsonator or drop roller, or molding, casting, or extrusion technologies.

Preferably, tablets including the taste masked particles are formed by compaction using a rotary tablet press as known in the art. In a rotary tablet press, a metered volume of particles is filled into a die cavity, which rotates as part of a "die table" from the filling position to a compaction position where the particles are compacted between an upper and a lower punch to an ejection position where the resulting tablet is pushed from the die cavity by the lower punch and guided to an ejection chute by a stationary "take-off" bar.

Preferably, tableting is carried out such that the chewable tablet is relatively soft. The hardness of the tablet is preferably up to about 15 kiloponds per square centimeter ($kp/cm^2$). More preferably, the hardness of the tablet is in the range of about 1 to about 8, most preferably about 2 to about 5, $kp/cm^2$. Hardness is a term used in the art to describe the diametral breaking strength as measured by conventional pharmaceutical hardness testing equipment, such as a Schleuniger Hardness Tester. In order to compare values across different size tablets, the breaking strength must be normalized for the area of the break. This normalized value, expressed in $kp/cm^2$, is sometimes referred in the art as tablet tensile strength. A general discussion of tablet hardness testing is found in Leiberman et al., *Pharmaceutical Dosage Forms—Tablets*, Volume 2, $2^{nd}$ ed., Marcel Dekker Inc., 1990, pp. 213–217, 327–329.

The active ingredient is present in the chewable tablet in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dose regime, the age and weight of the patient, and other factors must be considered.

The chewable tablet may contain other conventional ingredients such as fillers, including water soluble compressible carbohydrates such as sucrose, mannitol, sorbitol, maltitol, xylitol, lactose, and mixtures thereof; conventional dry binders including cellulose, cellulosic derivatives, polyvinyl pyrrolidone, starch, modified starch, and mixtures thereof, and in particular microcrystalline cellulose; sweeteners including aspartame, acesulfame potassium, sucralose and saccharin; and lubricants, such as magnesium stearate, stearic acid, talc, and waxes. The chewable tablet may also incorporate pharmaceutically acceptable adjuvants, including for example preservatives, flavors, antioxidants, surfactants, and coloring agents.

Tablets made according to the invention do not dissolve in the mouth, but rather dissolve in the upper regions of the gastro-intestinal tract. The release profile of taste masked particles according to the invention can also be varied by changing the ratio of enteric and insoluble film forming polymers in the coating formulation. In general however, the active ingredient in tablets made according to the invention is at least 80% dissolved in 30 minutes in pH 7.2 phosphate buffer when tested according to USP method II at 50 rpm, and is at least 70% dissolved in 60 minutes in pH 5.6 acetate buffer when tested according to USP method II at 50 rpm. Chewable tablets according to the invention therefore provide an improved combination of taste masking and immediate release characteristics.

Specific embodiments of the present invention are illustrated by way of the following examples. This invention is not confined to the specific limitations set forth in these examples, but rather to the scope of the appended claims. Unless otherwise stated, the percentages and ratios given below are by weight.

EXAMPLES

Example 1

Preparation of Comparative Particles

Ibuprofen was granulated with povidone, sodium lauryl sulfate, and sodium starch glycolate using purified water in a rotary fluid bed granulator according to the method disclosed in U.S. Pat. No. 5,320,855, the disclosure of which is hereby incorporated by reference. The ibuprofen granules were then coated with a 50:50 mixture of hydroxyethylcellulose (Natrosol® 250 L) and hydroxypropyl methylcellulose (Methocel® E5) in water to a 22% coating level by weight of the finished coated particles, according to the method disclosed in U.S. Pat. No. 5,320,855.

Example 2

Preparation of Tastemasked Particles of the Invention

A coating solution was prepared by dispersing cellulose acetate, hydroxypropyl methylcellulose phthalate (HPMCP-50), and polysorbate 80, in a solvent consisting of 85% acetone, and 15% water, so that the coating materials represented 10% of the finished solution as follows:

| Coating Solution: | |
| --- | --- |
| Ingredient | Weight Percent |
| Acetone | 5100 |
| Water | 900 |
| HPMCP-50 | 353.34 |
| Cellulose Acetate | 286.67 |
| Polysorbate 80 | 26.67 |
| Total | 6666.67 |

1800 g of ibuprofen powder and 200 g of microcrystalline cellulose (Avicel® PH101) were charged into a rotary fluid bed coater (Glatt GPCG-5). The powder bed was mobilized using a rotor speed of 300 rpm and air volume of 0.1–0.2 inches of water. The coating solution was sprayed onto the particles through tangentially oriented nozzles at a rate of 80 g per minute. Inlet air temperature was 42° C. After all of the solution was sprayed, the resulting coated particles were dried at a decreased rotor speed of 100 rpm for 8 minutes. The final dried batch weighed 2141 g (80% yield). The level of coating materials was 25% by weight of the total finished coated particles.

The resulting coated particles had an average diameter of 323 microns with a standard deviation of 122 microns according to a normal distribution model ($r^2$=0.984).

Example 3

In-Vitro Dissolution of Coated Particles

Dissolution of the particles of Examples 1 and 2 was tested by USP paddle method in pH 7.2 phosphate buffer at 50 rpm. 100% of the ibuprofen active ingredient was released from both sets of particles in less than 30 minutes.

Example 4

Preparation of Comparative Chewable Tablets

Coated particles from Example 1 (22% level of HPMC/HEC) were blended with aspartame, acesulfame potassium, citric acid, granular mannitol, fumaric acid, microcrystalline cellulose, and flavor in a plastic bag by inverting 100 times. Magnesium stearate was added, and the mixture was further blended by inverting 20 times.

| Ingredient | Amount (mg/tablet) |
|---|---|
| HPMC/HEC Coated Ibuprofen (76.25% active) | 131.1 |
| Aspartame NF | 11.55 |
| Acesulfame Potassium | 5.78 |
| Citric Acid USP, anhydrous | 2.00 |
| Mannitol USP, granular | 515 |
| Microcrystalline cellulose (Avicel PH101) | 77 |
| Fumaric Acid NF (fine granular) | 20 |
| Orange Flavor | 2 |
| Magnesium Stearate NF | 5.78 |
| TOTAL | 770.21 |

The resulting blend was compressed on a rotary tablet press at 40 rpm using 15/32" diameter flat faced beveled edge tablet tooling to an average tablet weight of 770.2 mg, tablet hardness of 3.2 kp, and tablet thickness of 0.24 inches. Friability by USP method was 2.7%.

Example 5

Preparation of Chewable Tablets of the Invention

Coated particles from Example 2 (25% level of CA/HPMCP-50/Polysorbate-80) were blended with aspartame, acesulfame potassium, citric acid, granular mannitol, fumaric acid, microcrystalline cellulose, and flavor in a plastic bag by inverting 100 times. Magnesium stearate was added, and the mixture was further blended by inverting 20 times.

| Ingredient | Amount (mg/tablet) |
|---|---|
| CA/HPMCP/Polysorbate-80 Coated Ibuprofen (67.5% active) | 148.1 |
| Aspartame NF | 11.55 |
| Acesulfame Potassium | 5.78 |
| Citric Acid USP, anhydrous | 2.00 |
| Mannitol USP, granular | 498 |
| Microcrystalline cellulose (Avicel PH101) | 77 |
| Fumaric Acid NF (fine granular) | 20 |
| Orange Flavor | 2 |
| Magnesium Stearate NF | 5.78 |
| TOTAL | 770.21 |

The resulting blend was compressed on a rotary tablet press at 40 rpm using 15/32" diameter flat faced beveled edge tablet tooling to an average tablet weight of 770.2 mg, tablet hardness of 3.2 kp, and tablet thickness of 0.25 inches. Friability by USP method was 2.2%.

Example 6

Evaluation of Chewable Tablets from Examples 4 and 5

The tablets prepared in Examples 4 and 5 were evaluated for the intensity of "throat burn," a characteristic taste property of ibuprofen. The tablets from Example 4 were found to have a high level of throat burn or catch with some lingering throat numbness. The tablets from Example 5 were perceived to have no throat burn.

Example 7

Preparation of Tastemasked Particles According to the Invention

A coating solution was prepared by dispersing cellulose acetate, hydroxypropyl methylcellulose phthalate (HPMCP-50), and hydroxypropyl cellulose (Klucel-EF) in a solvent consisting of 85% acetone, and 15% water, so that the coating materials represented 10% of the finished solution. The relative amounts of coating materials (as a percent of the final coating) were:

| | |
|---|---|
| Cellulose Acetate | 45% |
| HPMCP-50 | 35% |
| Hydroxypropyl cellulose | 20% |

The solution was used to coat a mixture of ibuprofen (80%), microcrystalline cellulose (10%), and fumaric acid (10%) according to the method in Example 2. The level of coating materials was 20% by weight of the total finished coated particles. The resulting coated particles had an average diameter of 166 microns, and a dissolution of 97% released at 60 minutes in pH 5.6 acetate buffer by USP method II at 50 rpm.

Example 8

Manufacture and Bioavailability Testing of Chewable Tablets

Chewable tablets incorporating the coated particles of Example 7 were compressed using a Manesty Beta rotary press. The selected unit dose formula for the tablets was as follows:

| Chewable Composition (100 mg Ibuprofen, Orange Flavor), Tablet Weight 770 mg | | |
|---|---|---|
| Ingredient | % | mg/tab |
| Encapsulated Ibuprofen* | | |
| FD&C Yellow No. 6 Aluminum Lake Color | 0.23 | 1.76 |
| Microcrystalline Cellulose (AVICEL PH-101 NF) (Flow aid) | 10.0 | 77.0 |
| Aspartame NF (Sweetener) | 1.5 | 11.55 |
| Acesulfame-K Sweetener | 0.75 | 5.78 |
| Fumaric Acid (Granular) (Acidulant) | 2.59 | 20 |
| Citric Acid USP (Flavor) | 0.26 | 2.0 |
| Natural Orange Flavor 5-11757 | 0.26 | 5.78 |
| Magnesium Stearate NF (Lubricant) | 0.75 | 5.77 |
| Mannitol USP (Granular) [FL2080] Filler) | | |
| TOTAL | 100.0 | 770.0 |

*Ibuprofen & Mannitol adjustment calculation based on Ibuprofen in coated particles.

The chewable tablets were manufactured using the following procedure:

1. The aspartame, acesulfame-K, citric acid, fumaric acid, microcrystalline cellulose, color, flavor, mannitol, ibuprofen were blended for 15 minutes in a twin shell blender (Patterson-Kelly Inc.). Magnesium stearate was added to the blended mixture, and the mixture was blended for an additional 5 minutes.

2. The resulting tablet blend was then compressed using a 15/32" round FFBE tooling using a rotary tablet press (Manesty Beta Press) to a target weight of 770 mg, hardness of 8.0 kp, and thickness of 5.90 mm.

The bioavailability of the chewable tablets (in comparison to Children's Motrin® Chewable Tablets, a reference product) was assessed in 16 healthy human volunteers according to an approved clinical protocol. The following pharmacokinetic parameters were evaluated: area under the plasma concentration-time curve (AUC), maximum plasma concentration ($C_{max}$), time required for peak plasma concentration ($T_{max}$) and, absorption half-time ($T_{1/2}$). The formula selected for the bioscan studies and the biostudy results are summarized in the following table.

Bioscan Results
(770 mg, 100 mg Ibuprofen, Orange Flavor)

| Tablet Composition and Physical Properties | | | | | | | | | |
|---|---|---|---|---|---|---|---|---|---|
| Tablet Properties | | Pharmacokinetic Parameters | | | | | | | |
| Average Hardness | Average Weight | *$C_{max}$ (ng/ml) | | *$T_{max}$ (Hours) | | *AUC (ng/ml-hr) | | *$T_{1/2}$ (Hours) | |
| (Kp) | (mg) | Ave | CV | Ave | CV | Ave | CV | Ave | CV |
| Reference Product 7.3 | 772 | 15.7 | 21.8 | 1.96 | 46.8 | 62.8 | 19.2 | 1.92 | 15.4 |
| Tablet according to the Invention 8.70 | 769.3 | 16.5 | 11.7 | 2.2 | 33.5 | 59.4 | 14.8 | 1.91 | 14.9 |

\* - Represent Average Values
CV - Coefficient of variation
NA - Not applicable

Example 9

Preparation of Tastemasked Particles According to the Invention

A coating solution (350 kg) was prepared by dispersing cellulose acetate, hydroxypropyl methylcellulose phthalate, and polysorbate 80 in a solvent consisting of 85% acetone, and 15% water, so that the coating materials represented 10% of the finished solution.

112 kg of ibuprofen powder, 7 kg of microcrystalline cellulose (Avicel® PH101), 7 kg of sodium starch glycolate, and 14 kg of fumaric acid, were charged into a rotary fluid bed coater (GlattGRG 200). The powder bed was mobilized using a rotor speed of 200 rpm, and air volume of 2400 CFM. The coating solution was sprayed onto the particles through tangentially oriented nozzles at an initial rate of 1200 g per minute. Inlet air temperature was 41° C. Particle size was monitored throughout the process. When the portion of the particles less than 125 microns decreased to less than 20% (approximately 175 kg of solution had been sprayed), the spray rate was reduced to 1000 g/min. When the portion of the particles less than 125 microns decreased to less than 15% (approximately 235 kg of solution had been sprayed), the spray rate was reduced to 800 g/minute. After all of the solution was sprayed, the resulting coated particles were dried at a rotor speed of 100 rpm until the product temperature reached 38° C. (3–5 minutes). The final dried batch weighed 155.7 kg (91% yield). Total processing time was less than 6 hours.

The level of coating materials was 20% by weight of the total finished coated particles. Approximately 75% of the finished coated particles were between 150 and 420 microns in size. Greater than 90% of the active ibuprofen was dissolved in 45 minutes in pH 7.2 phosphate buffer by USP paddle method at 50 rpm.

We claim:

1. A taste masked particle comprising a core containing an active ingredient and a continuous polymeric coating covering said core, said coating comprising a mixture of a) an enteric polymer selected from the group consisting of hydroxypropyl metyylcellulose phthalate, hydroxypropy methlcellulose aoeate succinate, cellulose acetate phthalate, polyvinylacetate phthalate, and mixtures thereof; and b) a water insoluble, cellulosic film forming polymer selected from the group consisting of celulose acetate, ethylcellulose, and mixtures thereof, wherein the active ingredient is a nonsteroidal anti-inflammatory drug and is at mixtures thereof, least 80% dissolved in 30 minutes in pH 7.2 phosphate buffer when tested according to USP method II at 50 rpm and is at least 70% dissolved in 60 minutes in pH 5.6 acetate buffer when tested according to USP method II at 50 rpm, wherein the weight ratio of enteric polymer to water insoluble film forming polymer in the coating is in the range of about 20:80 to about 80:20.

2. The particle of claim 1, wherein the surface of said particle is substantially free of active ingredient.

3. The particle of claim, wherein the coating is substantially free of plasticizer.

4. The particle of claim 1, wherein the active ingredient is a nonsteroidal anti-inflammatory drug selected from the group consisting of ibuprofen, ketoprofen, flurbiprofen, naproxen, diclofenac, rofecoxib, celecoxlb, aspirin, pharmaceutically acceptable salts and metabolites thereof, and mixtures thereof.

5. The particle of claim 1, wherein active ingredient is ibuprofen.

6. A taste masked particle comoprising a core containing an active ingredient and a continuous polymeric coating covering said core, said coating comprising a mixture of a) an enteric polymer selected from the group consisting of hydroxypropyl methylcellulose phthalate, hydroxypropyl methylcellulose acetate succinate, cellulose acetate phthalate, and mixturese thereof; and b) a cellulose acetate, wherein the active ingredient is a nonsteroidal anti- inflammatory drug and is at least 80% dissolved in 30 minutes in pH 7.2 phosphate buffer when tested according to USP method II at 50 rpm and is at least 70% dissolved in 60 minutes in pH 5.6 acetate buffer when tested according to USP method II at 50 rpm.

7. The particle of claim 1 further comprising a non-enteric, water soluble polymer.

8. The particle of claim 1 further comprising a surfactant.

9. A method of taste masking particles comprising an active ingredient, which comprises applying a continuous polymeric coating over said particles, said coating comprising a mixture of a) an enteric polymer selected from the group consisting of hydroxypropyl metyylcellulose phthalate, hydroxypropy methlcellulose aoeate succinate, cellulose acetate phthalate, polyvinylacetate phthalate, and mixtures thereof; and b) a water insoluble, cellulosic film forming polymer selected from the group consisting of celulose acetate, ethylcellulose, poly(ethyl acrylate, methyl methacrylate, trimethylammonloethyl methacrylate chloride), wherein the active ingredient is a nonsteroidal anti-inflammatory drug and is at mixtures thereof, least 80% dissolved in 30 minutes in pH 7.2 phosphate buffer when tested according to USP method II at 50 rpm and is at least 70% dissolved in 60 minutes in pH 5.6 acetate buffer when tested according to USP method II at 50 rpm, wherein the weight ratio of enteric polymer to water insoluble film forming polymer in the coating is in the range of about 20:80 to about 80:20.

10. The method of claim 9 wherein the coating is substantially free of plasticizer.

11. The method of claim 9, wherein the active ingredient is a nonsteroidal anti-inflammatory drug selected from the group consisting of ibuprofen, ketoprofen, flurbiprofen naproxen, diclofenac, rofecoxib, celecoxib, aspirin, pharmaceutically acceptable salts and metabolites thereof, and mixtures thereof.

12. The method of claim 9, wherein the enteric polymer is selected from the group consisting of hydroxypropyl methylcellulose phthalate, hydroxypropyl methylcellulose acetate succinate and cellulose acetate phthalate, and mixtures thereof.

13. The method of claim 9, wherein the water insoluble film forming polymer is selected from the group consisting of cellulose acetate, ethylcellulose, and mixtures thereof.

14. A chewable tablet comprising taste masked particle, each particle comprising a core containing an active ingredient and a continuous polymeric coating covering said core, said coating comprising a mixture of a) an enteric polymer selected from the group consisting of hydroxypropyl metyylcellulose phthalate, hydroxypropy methlcellulose aoeate succinate, cellulose acetate phthalate, polyvinylacetate phthalate, and mixtures thereof; and b) a water insoluble, cellulosic film forming polymer selected from the group consisting of celulose acetate, ethylcellulose, poly (ethyl acrylate, methyl methacrylate, trimethylammonieothyl methacrylate chloride), and mixtures thereof, wherein the active ingredient is a nonsteroidal anti-inflammatory drug and is at mixtures thereof, least 80% dissolved in 30 minutes in pH 7.2 phosphate buffer when tested according to USP method II at 50 rpm and is at least 70% dissolved in 60 minutes in pH 5.6 acetate buffer when tested according to USP method II at 50 rpm, wherein the weight ratio of enteric polymer to water insoluble film forming polymer in the coating is in the range of about 20:80 to about 80:20.

15. The chewable tablet of claim 14, wherein the enteric polymer is selected from the group consisting of hydroxypropyl methylcellulose phthalate, hydroxypropyl methylcellulose acetate succinate, cellulose acetate phthalate, and mixtures thereof.

16. The chewable tablet of claim 14, wherein the water insoluble, cellulosic film forming polymer is selected from the group consisting of cellulose acetate, ethylcellulose, and mixtures thereof.

17. The chewable tablet of claim 14, wherein said coating further comprises an ingredient selected from the group consisting of non-enteric, water soluble polymers and surfactants.

18. The chewable tablet of claim 14, wherein the surfaces of the particles are substantially free of active ingredient.

19. The chewable tablet of claim 14, wherein the coating is substantially free of plasticizer.

20. The chewable tablet of claim 14, wherein the active ingredient is a nonsteroidal anti-inflammatory drug selected from the group consisting of ibuprofen, ketoprofen, flurbiprofen, naproxen, diclofenac, rofecoxib, celecoxib, aspririn, pharmaceutically acceptable salts and metabolites thereof, and mixtures thereof.

* * * * *